United States Patent
Huang

(10) Patent No.: US 10,092,375 B2
(45) Date of Patent: Oct. 9, 2018

(54) INVISIBLE ORTHODONTIC APPLIANCE WITH MOLAR DISTALIZATION DEVICE

(71) Applicant: Jialiang Huang, Shanghai (CN)

(72) Inventor: Jialiang Huang, Shanghai (CN)

( * ) Notice: Subject to any disclaimer, the term of this patent is extended or adjusted under 35 U.S.C. 154(b) by 0 days.

(21) Appl. No.: 15/617,687

(22) Filed: Jun. 8, 2017

(65) Prior Publication Data

US 2018/0256295 A1  Sep. 13, 2018

(30) Foreign Application Priority Data

Mar. 9, 2017 (CN) .......................... 2017 1 0137953

(51) Int. Cl.
*A61C 3/00* (2006.01)
*A61C 7/08* (2006.01)
*A61C 7/10* (2006.01)

(52) U.S. Cl.
CPC . *A61C 7/08* (2013.01); *A61C 7/10* (2013.01)

(58) Field of Classification Search
CPC .................................. A61C 7/08; A61C 7/10
USPC ...................................................... 433/8–24
See application file for complete search history.

(56) References Cited

U.S. PATENT DOCUMENTS

| | | | | | |
|---|---|---|---|---|---|
| 3,293,747 | A | * | 12/1966 | Denholtz | A61C 7/00 433/21 |
| 5,022,855 | A | * | 6/1991 | Jeckel | A61C 7/00 433/18 |
| 5,092,768 | A | * | 3/1992 | Korn | A61C 7/00 433/18 |
| 7,357,635 | B2 | * | 4/2008 | Belfor | A61C 7/00 433/24 |
| 2008/0233529 | A1 | * | 9/2008 | Kuo | A61C 7/08 433/6 |
| 2015/0079530 | A1 | * | 3/2015 | Bergersen | A61C 7/08 433/6 |
| 2018/0071054 | A1 | * | 3/2018 | Ha | A61C 7/006 |

* cited by examiner

*Primary Examiner* — Matthew Nelson
(74) *Attorney, Agent, or Firm* — Muncy, Geissler, Olds & Lowe, P.C.

(57) ABSTRACT

The present invention provides an invisible orthodontic appliance with a molar distalization device, comprising an orthodontic invisible aligner, and further comprising a molar distalization device arranged on the orthodontic invisible aligner, wherein the molar distalization device comprises a lip bumper arranged just in front of the orthodontic invisible aligner close to the lip side, and a connector connected with the lip bumper, and the end of the connector is connected to the molar position of the orthodontic invisible aligner. The end of the connector forms a U-shaped structure and the tail end of the U-shaped structure is connected to the molar position of the orthodontic invisible aligner. The novel orthodontic appliance provided by the present invention has the advantages of ensuring the attractiveness and greatly improving the orthodontic effect, improving the orthodontic speed and shortening the service cycle of the aligner.

11 Claims, 2 Drawing Sheets

INVISIBLE ORTHODONTIC APPLIANCE WITH MOLAR DISTALIZATION DEVICE

BACKGROUND

Technical Field

The present invention is directed to an orthodontic appliance for use in oral medicine, and more particularly to an invisible orthodontic appliance with a molar distalization device.

Related Art

As usual, when people are 13 to 14 years old, a total of 28 permanent teeth will grow out, and sequentially comprises central incisors, lateral incisors, canines, first premolars, second premolars, first molars and second molars from the middle to both sides. And wisdom teeth (third molars) will grow out when people are about 17 to 25 years old. In the orthodontic process, the molars distally move to open up a gap for aligning teeth or retracting upper anterior teeth.

The orthodontic appliance is a tool for aligning teeth. The traditional orthodontic appliance is usually made of metal, and attached to the teeth to move and align the teeth by exerting a slight force on the teeth. But because its metal shape is not beautiful, the traditional orthodontic appliance is gradually replaced with the invisible orthodontic appliance recently. A full set of clear plastic is produced by simulating the alignment process and tooth movement with a computer to exert a force on the teeth to gradually align the teeth. However, the existing invisible orthodontic appliance has the problems of slow speed and long cycle during molar distalization, and needs to additionally use an orthodontic appliance for molar distalization. And the molars are moved by generally using an implant anchorage, a face bow and other ways in the traditional orthodontics, but also the implant anchorage and the face bow are made of a metal material, which is inconvenient to use and unattractive.

SUMMARY

The present invention provides an invisible orthodontic appliance with a molar distalization device, and aims to solve the traditional technical problems that the invisible orthodontic appliance has a slow orthodontic speed and a long cycle.

The invisible orthodontic appliance with the molar distalization device comprises an orthodontic invisible aligner, and further comprises a molar distalization device arranged on the orthodontic invisible aligner, wherein the molar distalization device comprises a lip bumper arranged in front of the orthodontic invisible aligner close to the lip side, and the connector connected with the lip bumper, and the end of the connector is connected to the molar position of the orthodontic invisible aligner.

Further, the end of the connector forms a U-shaped structure and the tail end of the U-shaped structure is connected to the molar position of the orthodontic invisible aligner.

Further, the molar distalization device is made of a resilient transparent polymeric material.

Further, the molar distalization device is detachably connected with the orthodontic invisible aligner.

Further, the molar distalization device and the orthodontic invisible aligner are integrated.

Further, a cutting area is reserved at a joint of the connector of the molar distalization device and the orthodontic invisible aligner.

Further, a gap is arranged between the lip bumper and the orthodontic invisible aligner.

Further, the lip bumper is in a single-piece form, and a groove is formed in the upper part of the lip bumper.

Further, the lip bumper is of a double-piece structure, the two pieces of lip bumper are arranged horizontally and symmetrically along the center line of the orthodontic invisible aligner and a vertical gap is arranged between the two pieces of lip bumper.

Further, the molar distalization device is a single-sided molar distalization device, wherein one end of the lip bumper is connected with the anterior tooth position at front part of the orthodontic invisible aligner, the other end of the lip bumper is connected with the connector, and the end of the connector is connected to the molar position of the orthodontic invisible aligner.

The novel orthodontic appliance provided by the present invention has the advantages of ensuring the attractiveness and greatly improving the orthodontic effect, improving the orthodontic speed and shortening the service cycle of the aligner. The advantages of the present invention are embodied in the following aspects:

The molars distalization in a way that the lip bumper is matched with the connector, under certain training, the force of the upper lip and lower lip acts on the lip bumper, and acts on the molars needing distalization through a connector structure. But also a role in strengthening the anchorage of posterior teeth is played.

The overall structure is made of a transparent polymeric material, and different from the traditional metal orthodontic appliance, and has an 'invisible' effect. Meanwhile, the molar distalization device and the orthodontic invisible aligner are of a detachable structure. In some special or inconvenient circumstances, the molar distalization device can be detached, and the orthodontic invisible aligner can be used alone. The molar distalization device and the orthodontic invisible aligner can also be fixedly integrated, and an area to be cut can be arranged at a joint of the two, which is convenient to flexibly adjust, so that the device can be used in the early stage, and the molar distalization device can be removed according to the orthodontic situation in the later stage.

The end of the molar distalization device keeps the direction of acting force backward through the U-shaped structure, thus bringing backward thrust into full play.

The certain gap is arranged between the lip bumper and the orthodontic invisible aligner, that is, a certain distance is kept between the lip bumper and teeth, so that the lip bumper is in full contact with the lip to bear force.

It has been proved by clinical trials that the orthodontic speed of the invisible orthodontic appliance provided by the present invention is 2 to 5 times faster than that of the ordinary orthodontic invisible aligner, and the effect is obvious.

The orthodontic appliance with the single-sided molar distalization device is also provided to be used for distalization of the single-sided molars and alignment of the single-sided teeth in a targeted way.

DETAILED DESCRIPTION

The present invention is further illustrated by the following embodiments:

Embodiment 1 (Take an Upper Orthodontic Appliance for Example)

Figure 1:
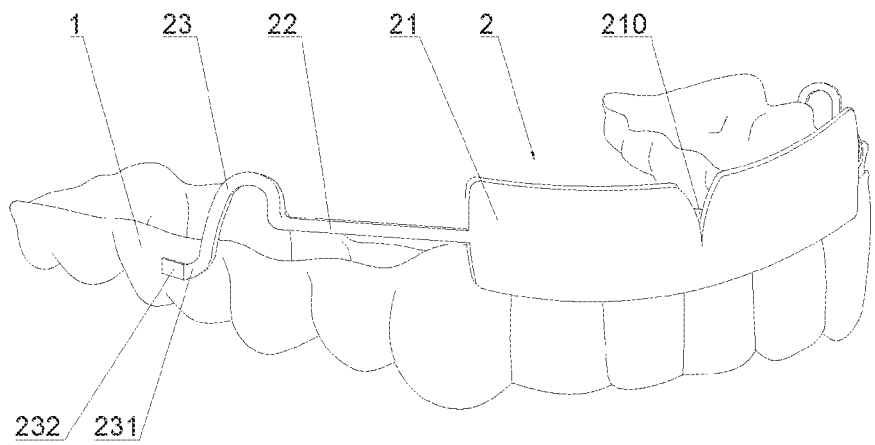
FIG. 1 is a schematic view of an invisible orthodontic appliance with a molar distalization device as described in an embodiment 1.
Figure 3:
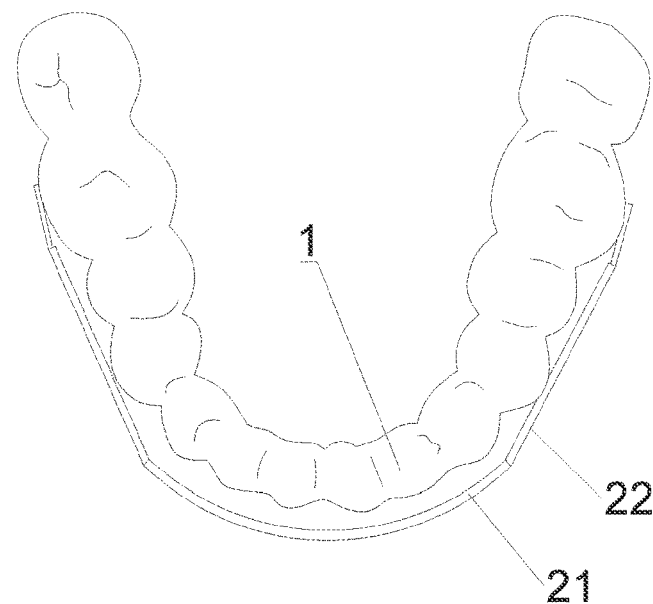
FIG. 3 is a bottom schematic view of the invisible orthodontic appliance with the molar distalization device as described in the embodiment 1.
Figure 4:
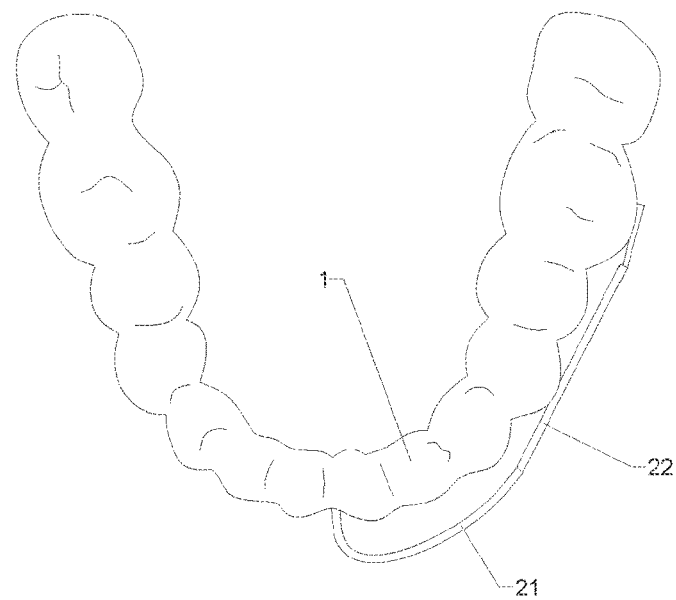
FIG. 4 is a bottom schematic view of the invisible orthodontic appliance with the molar distalization device as described in an embodiment 3.

Referring to FIG. 1 and FIG. 3, an invisible orthodontic appliance with a molar distalization device comprises an orthodontic invisible aligner 1 and a molar distalization device 2 which are made of a resilient transparent polymeric material. The molar distalization device 2 comprises a lip bumper 21 arranged in the upper position just in front of the orthodontic invisible aligner and connectors 22 connected to two sides of the lip bumper 21, and the end of the connector 22 forms a U-shaped structure 23; a U-shaped slot of the U-shaped structure 23 is arranged downwardly, and the tail end of the U-shaped structure 23 is connected to the molar position of the orthodontic invisible aligner 1. The molar distalization device 2 and the orthodontic invisible aligner 1 are inserted into a connector slot 232 in the side of the orthodontic invisible aligner through a hook-shaped structure 231 at the tail of the connector 22 to form a detachable connection. A gap is arranged between the lip bumper 21 and the orthodontic invisible aligner 1. The lip bumper 21 is in a single-piece form, and a groove 210 is formed in the upper part of the lip bumper 21 and corresponds to a labial frenum in position.

Embodiment 2 (Take an Upper Orthodontic Appliance for Example)

Figure 2:
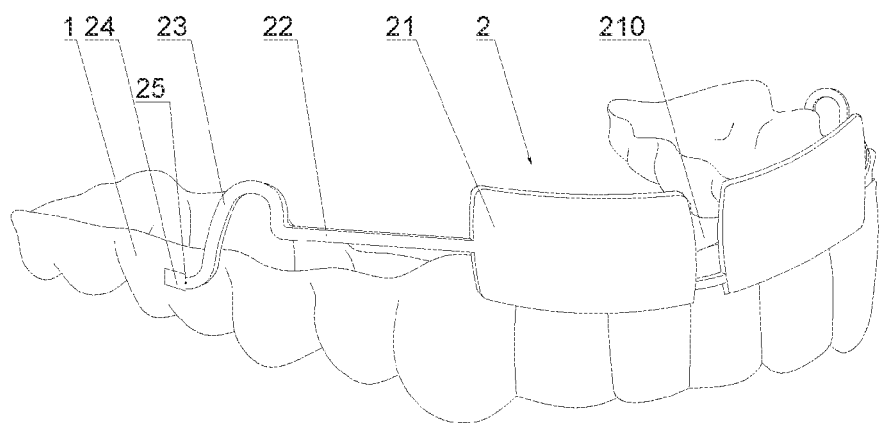
FIG. 2 is a schematic view of the invisible orthodontic appliance with the molar distalization device as described in an embodiment 2.

Referring to FIG. 2, an invisible orthodontic appliance with a molar distalization device comprises invisible aligner 1 and a molar distalization device 2 which are made of a resilient transparent polymeric material.

The molar distalization device 2 comprises a lip bumper 21 arranged in the upper position just in front of the orthodontic invisible aligner and connectors 22 connected with the lip bumper 21, and the end of the connector 22 forms a U-shaped structure 23; a U-shaped slot of the U-shaped structure 23 is arranged downwardly, and the tail end of the U-shaped structure 23 is connected to the molar position of the orthodontic invisible aligner 1. The molar distalization device 2 and the orthodontic invisible aligner 1 are integrated, a thinner cutting area 24 is reserved at a joint of the connector 22 of the molar distalization device and the orthodontic invisible aligner 1, and a line to be cut 25 is arranged on the cutting area 24. A gap is arranged between the lip bumper 21 and the orthodontic invisible aligner 1. The lip bumper 21 is of a double-piece structure, the two pieces of lip bumper 21 are arranged horizontally and symmetrically along the center line of the orthodontic invisible aligner and a vertical gap is arranged between the two pieces of lip bumper 21.

Embodiment 3 (Take an Upper Orthodontic Appliance for Example)

An invisible orthodontic appliance with a molar distalization device comprises orthodontic invisible aligner 1 and the molar distalization device 2 which are made of a resilient transparent polymeric material.

The molar distalization device 2 is a single-sided molar distalization device, comprising a lip bumper 21 and connectors 22 connected with the lip bumper 21, wherein one end of the lip bumper 21 is inwardly bent and connected with the front tooth position at front part of the orthodontic invisible aligner 1, and the other end of the lip bumper 21 is connected with the connector 22; the tail end of the connector 22 forms a U-shaped structure 23, and a U-shaped slot of the U-shaped structure 23 is arranged downwardly; the tail end of the U-shaped structure 23 is connected to the molar position of the orthodontic invisible aligner 1. The molar distalization device 2 and the orthodontic invisible aligner 1 are integrated, a thinner cutting area 24 is reserved at a joint of the connector 22 of the molar distalization device and the orthodontic invisible aligner 1, and a line to be cut 25 is arranged on the cutting area 24. A gap is arranged between the lip bumper 21 and the orthodontic invisible aligner 1.

The description of the present invention has been set forth in detail above. It is not intended to limit the present invention to the disclosed forms and ways. Corresponding modifications or changes can be made according to the above ways. The discussions on embodiments are intended to better illustrate the principles of the present invention and its utility so as to utilize the present invention to make various modifications and to meet other specific needs. All such modifications and changes should be interpreted in accordance with the fair and legitimate rights and fall within the scope of the present invention in accordance with the appended claims.

What is claimed is:

1. An invisible orthodontic appliance with a molar distalization device, comprising an orthodontic invisible aligner, and characterized by further comprising a molar distalization device arranged on the orthodontic invisible aligner, wherein the molar distalization device comprises a lip bumper arranged in front of the orthodontic invisible aligner close to the lip side, and a connector connected with the lip bumper, and the end of the connector is connected to the molar position of the orthodontic invisible aligner.

2. The invisible orthodontic appliance with the molar distalization device according to claim 1, characterized in that the end of the connector forms a U-shaped structure and the tail end of the U-shaped structure is connected to the molar position of the orthodontic invisible aligner.

3. The invisible orthodontic appliance with the molar distalization device according to claim 2, characterized in that the molar distalization device is made of a resilient transparent polymeric material.

4. The invisible orthodontic appliance with the molar distalization device according to claim 3, characterized in that the molar distalization device is detachably connected with the orthodontic invisible aligner.

5. The invisible orthodontic appliance with the molar distalization device according to claim 3, characterized in that the molar distalization device and the orthodontic invisible aligner are integrated.

6. The invisible orthodontic appliance with the molar distalization device according to claim 5, characterized in that a cutting area is reserved at a joint of the connector of the molar distalization device and the orthodontic invisible aligner.

7. The invisible orthodontic appliance with the molar distalization device according to claim 3, characterized in that the molar distalization device is a single-sided molar distalization device, wherein one end of the lip bumper is connected with the anterior tooth position at front part of the orthodontic invisible aligner, the other end of the lip bumper is connected with the connector, and the end of the connector is connected to the molar position of the orthodontic invisible aligner.

8. The invisible orthodontic appliance with the molar distalization device according to any one of claim 1, characterized in that a gap is arranged between the lip bumper and the orthodontic invisible aligner.

9. The invisible orthodontic appliance with the molar distalization device according to claim 8, characterized in that the lip bumper is in a single-piece form, and a groove is formed in the upper part of the lip bumper.

10. The invisible orthodontic appliance with the molar distalization device according to claim 8, characterized in that the lip bumper is of a double-piece structure, the two pieces of lip bumper are arranged horizontally and symmetrically along the center line of the orthodontic invisible aligner and a vertical gap is arranged between the two pieces of lip bumper.

11. The invisible orthodontic appliance with the molar distalization device according to claim 1, characterized in that the molar distalization device is a single-sided molar distalization device, wherein one end of the lip bumper is connected with the anterior tooth position at front part of the orthodontic invisible aligner, the other end of the lip bumper is connected with the connector, and the end of the connector is connected to the molar position of the orthodontic invisible aligner.

\* \* \* \* \*

UNITED STATES PATENT AND TRADEMARK OFFICE
CERTIFICATE OF CORRECTION

PATENT NO. : 10,092,375 B2  
APPLICATION NO. : 15/617687  
DATED : October 9, 2018  
INVENTOR(S) : Jialiang Huang et al.

Page 1 of 1

It is certified that error appears in the above-identified patent and that said Letters Patent is hereby corrected as shown below:

On the Title Page

Item (12), should read:  
--Huang et al.--

Item (72), should read:  
--Jialiang Huang, Shanghai (CN)  
Anqi Liu, Shanghai (CN)--

Signed and Sealed this  
First Day of February, 2022

Drew Hirshfeld  
*Performing the Functions and Duties of the*  
*Under Secretary of Commerce for Intellectual Property and*  
*Director of the United States Patent and Trademark Office*